US010206655B2

(12) United States Patent
Woo et al.

(10) Patent No.: US 10,206,655 B2
(45) Date of Patent: Feb. 19, 2019

(54) ULTRASONIC IMAGING APPARATUS AND CONTROL METHOD THEREOF

(71) Applicant: SAMSUNG MEDISON CO., LTD., Hongcheon-gun, Gangwon-do (KR)

(72) Inventors: Kyeong Gu Woo, Suwon-si (KR); Eun Ho Yang, Seoul (KR); Yeon Ho Kim, Seongnam-si (KR); Gil-Ju Jin, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 660 days.

(21) Appl. No.: 14/701,112

(22) Filed: Apr. 30, 2015

(65) Prior Publication Data
US 2016/0183920 A1    Jun. 30, 2016

(30) Foreign Application Priority Data
Dec. 30, 2014 (KR) .................. 10-2014-0193312

(51) Int. Cl.
*A61B 8/00* (2006.01)
*A61B 8/14* (2006.01)
*A61B 8/08* (2006.01)
*A61B 6/10* (2006.01)

(52) U.S. Cl.
CPC ............ *A61B 8/4405* (2013.01); *A61B 6/105* (2013.01); *A61B 8/461* (2013.01); *A61B 8/465* (2013.01); *A61B 8/467* (2013.01); *A61B 8/5292* (2013.01); *A61B 8/54* (2013.01); *A61B 8/56* (2013.01); *A61B 6/10* (2013.01); *A61B 8/4245* (2013.01); *A61B 8/4281* (2013.01); *A61B 8/4427* (2013.01); *A61B 8/565* (2013.01)

(58) Field of Classification Search
CPC ......... A61B 6/10; A61B 6/105; A61B 8/4245; A61B 8/4281; A61B 8/4405; A61B 8/4427; A61B 8/461; A61B 8/465; A61B 8/467; A61B 8/5292; A61B 8/54; A61B 8/56; A61B 8/565
See application file for complete search history.

(56) References Cited

U.S. PATENT DOCUMENTS

| 2012/0289829 A1 | 11/2012 | Barnes et al. |
| 2013/0197364 A1 | 8/2013 | Han |
| 2014/0323870 A1* | 10/2014 | Satsuka .................. A61B 8/56 600/459 |

FOREIGN PATENT DOCUMENTS

JP    2009-034305 A    2/2009

* cited by examiner

*Primary Examiner* — Michael Rozanski
(74) *Attorney, Agent, or Firm* — Morgan, Lewis & Bockius LLP

(57) ABSTRACT

Disclosed herein is an ultrasonic imaging apparatus of displaying functions related to the ultrasonic imaging apparatus on a display unit when the ultrasonic imaging apparatus moves, and activating a function selected by a user from among the functions displayed on the display unit. According to an embodiment, the ultrasonic imaging apparatus includes: a display unit configured to display one or more functions related to movement of the ultrasonic imaging apparatus when the ultrasonic imaging apparatus moves; and a controller configured to activate a function selected by a user from among the one or more functions displayed on the display unit.

10 Claims, 6 Drawing Sheets

FIG. 5

```
MOVEMENT MODE ON

A) WOULD YOU USE MOVEMENT MODE?
☐ POWER OFF WIRELESS PROBE
☐ ARRANGE PROBE CABLE
☐ UNLOCK CASTORS
☐ LOCK TO PREVENT MOVEMENT OF MONITOR
☐ POWER-SAVING FUNCTION
☐ SHOCK ABSORBING DEVICE
☐ STORE IMAGES
☑ STORE & TRANSMIT IMAGES
☑ NOTIFY WHEN NUMBER OF RECOGNIZED (WIRED/WIRELESS) PROBES IS
   DIFFERENT FROM NUMBER OF PROBES INSTALLED IN HOLDER
☑ NOTIFY EXISTENCE/ABSENCE OF GEL IN SYSTEM
☐ NOTIFY PLUGGING OUT LAN OR POWER CABLE

B) WOULD YOU APPLY THESE TO MOVEMENT MODE?
```

ULTRASONIC IMAGING APPARATUS AND CONTROL METHOD THEREOF

CROSS-REFERENCE TO RELATED APPLICATION

This application claims the benefit of Korean Patent Application No. 10-2014-0193312, filed on Dec. 30, 2014 in the Korean Intellectual Property Office, the disclosure of which is incorporated herein by reference.

BACKGROUND

1. Field

Embodiments of the present disclosure relate to an ultrasonic imaging apparatus for creating images about the inside of an object using ultrasonic waves.

2. Description of the Related Art

An ultrasonic imaging apparatus irradiates ultrasonic signals to a target region of an object from the surface of the object, and receives ultrasonic signals (ultrasonic echo signals) reflected from the target region so as to non-invasively acquire slice images about soft tissue of the object or images about blood vessels of the object based on information of the ultrasonic echo signals.

The ultrasonic imaging apparatus has advantages that it is a compact, low-priced apparatus and it can display images in real time, compared to other medical imaging apparatuses, such as an X-ray diagnostic apparatus, a X-ray Computerized Tomography (CT) scanner, a Magnetic Resonance Image (MRI) apparatus, and a nuclear medical diagnostic apparatus. Also, the ultrasonic imaging apparatus has high safety since there is no risk for patients to be exposed to radiation such as X-rays. For the advantages, the ultrasonic imaging apparatus is widely used to diagnose the heart, abdomen, urinary organs, uterus, etc.

The ultrasonic imaging apparatus includes an ultrasound probe to transmit ultrasonic signals to an object and to receive ultrasonic echo signals reflected from the object, in order to acquire an ultrasound image of the object, and a main body to create images about the inside of the object using the ultrasonic echo signals received from the ultrasound probe.

SUMMARY

Therefore, it is an aspect of the present disclosure to provide an ultrasonic imaging apparatus of displaying functions related to the ultrasonic imaging apparatus on a display unit when the ultrasonic imaging apparatus moves, and activating a function selected by a user from among the functions displayed on the display unit.

Additional aspects of the disclosure will be set forth in part in the description which follows and, in part, will be obvious from the description, or may be learned by practice of the disclosure.

In accordance with one aspect of the present disclosure, an ultrasonic imaging apparatus including: a display unit configured to display one or more functions related to movement of the ultrasonic imaging apparatus when the ultrasonic imaging apparatus moves; and a controller configured to activate a function selected by a user from among the one or more functions displayed on the display unit.

The ultrasonic imaging apparatus may further include a sensor configured to sense movement of the ultrasonic imaging apparatus, wherein if the sensor senses movement of the ultrasonic imaging apparatus, the display unit may display the one or more functions related to movement of the ultrasonic imaging apparatus.

The sensor may include at least one of an accelerometer, a gyro sensor, a position sensor, a motion sensor, or an infrared sensor, which is configured to sense movement of the ultrasonic imaging apparatus.

The ultrasonic imaging apparatus may further include an input unit configured to receive a command for setting a movement mode of the ultrasonic imaging apparatus, wherein if the input unit receives the command for setting the movement mode, the display unit may display the one or more functions related to movement of the ultrasonic imaging apparatus.

The input unit may include at least one of a mechanical type button, an electronic type button, or a touch button to allow a user to input the command for setting the movement mode.

The ultrasonic imaging apparatus may further include a notifying unit configured to notify movement of the ultrasonic imaging apparatus when the ultrasonic imaging apparatus moves.

The notifying unit may include at least one of a speaker configured to notify movement of the ultrasonic imaging apparatus through sound, a lamp configured to notify movement of the ultrasonic imaging apparatus through light, and a vibrator configured to notify movement of the ultrasonic imaging apparatus through vibrations.

The display unit may display text or an image to notify movement of the ultrasonic imaging apparatus when the ultrasonic imaging apparatus moves.

The one or more functions related to movement of the ultrasonic imaging apparatus may include at least one function among a power-off/power-saving function for a wireless probe, a power-off/power-saving function for the ultrasonic imaging apparatus, a castor unlock function, a lock function for preventing movement of the display unit, a function of recognizing installation of a registered probe, a function of recognizing existence/absence of gel, a shock absorbing function, and an ultrasound image storage and transmission function.

If the ultrasound image storage and transmission function is selected by a user, the controller may store at least one image transmitted to a Picture Archiving and Communication System (PACS) before the ultrasonic imaging apparatus moves, and transmit images acquired after the stored image to the PACS if the ultrasonic imaging apparatus is again connected to the PACS.

The ultrasonic imaging apparatus may further include a holder in which the probe and the gel are contained, the holder including a sensor configured to sense the probe and the gel.

When the ultrasonic imaging apparatus moves, the display unit may display a list of tasks needed for movement of the ultrasonic imaging apparatus.

The list of tasks may include a task of plugging out a Local Area Network (LAN) line or a power cable or a task of arranging a probe cable.

If a function is selected by a user from among the one or more functions displayed on the display unit, the display unit may display a message requesting confirmation on activation of the selected function.

In accordance with another aspect of the present disclosure, a method of controlling an ultrasonic imaging apparatus includes: displaying one or more functions related to movement of the ultrasonic imaging apparatus when the ultrasonic imaging apparatus moves; and activating a function selected by a user from among the one or more functions displayed on the display unit.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 5 shows functions related to movement of an ultrasonic imaging apparatus according to an embodiment of the present disclosure, which are displayed on a display unit of the ultrasonic imaging apparatus.

DETAILED DESCRIPTION

Hereinafter, an ultrasonic imaging apparatus and a control method thereof according to embodiments of the present disclosure will be described in detail with reference to the accompanying drawings.

Hereinafter, embodiments of the present disclosure will be described in detail with reference to the accompanying drawings.

Figure 1:
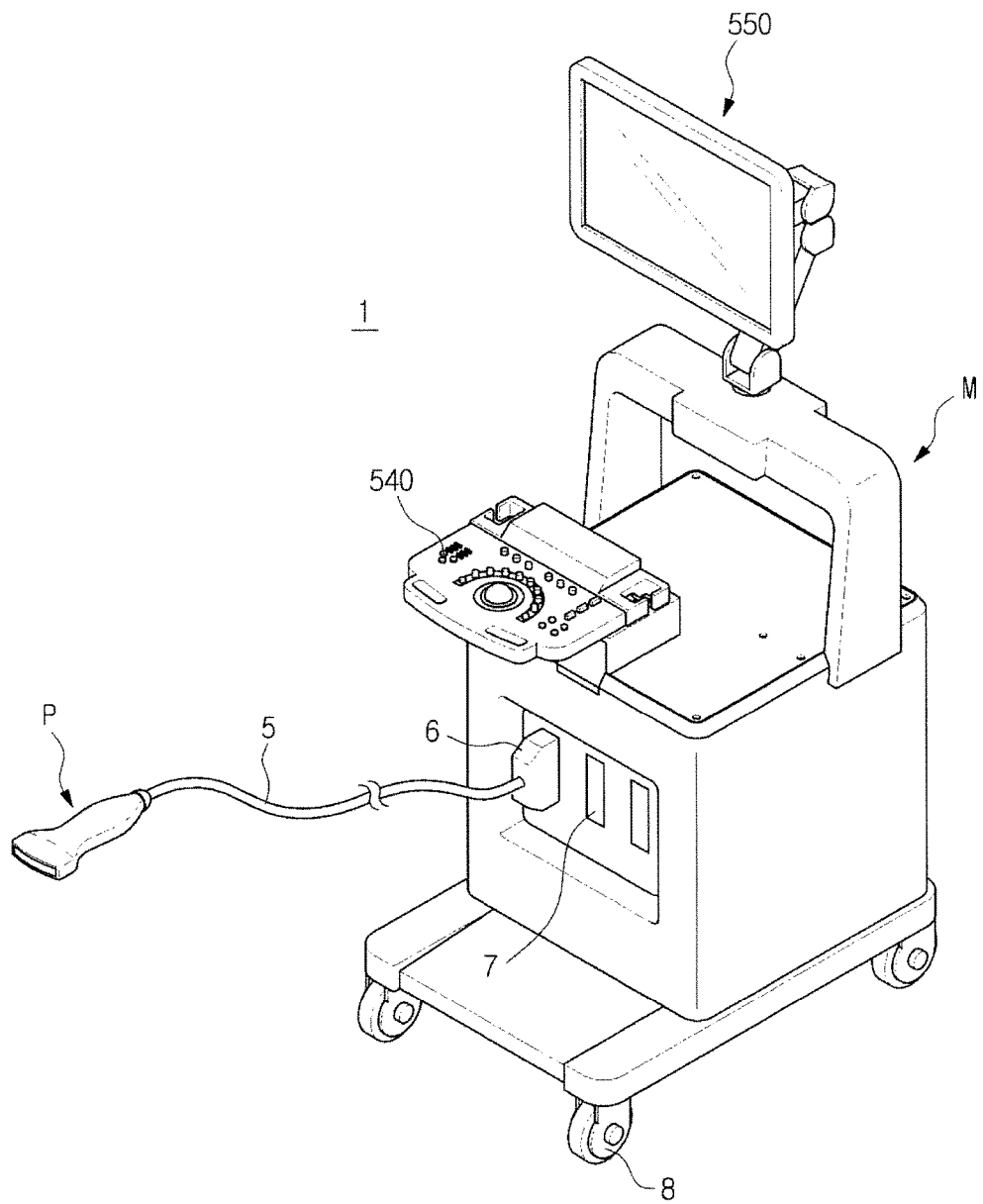
FIG. 1 shows an external appearance of an ultrasonic imaging apparatus according to an embodiment of the present disclosure.
Figure 2:
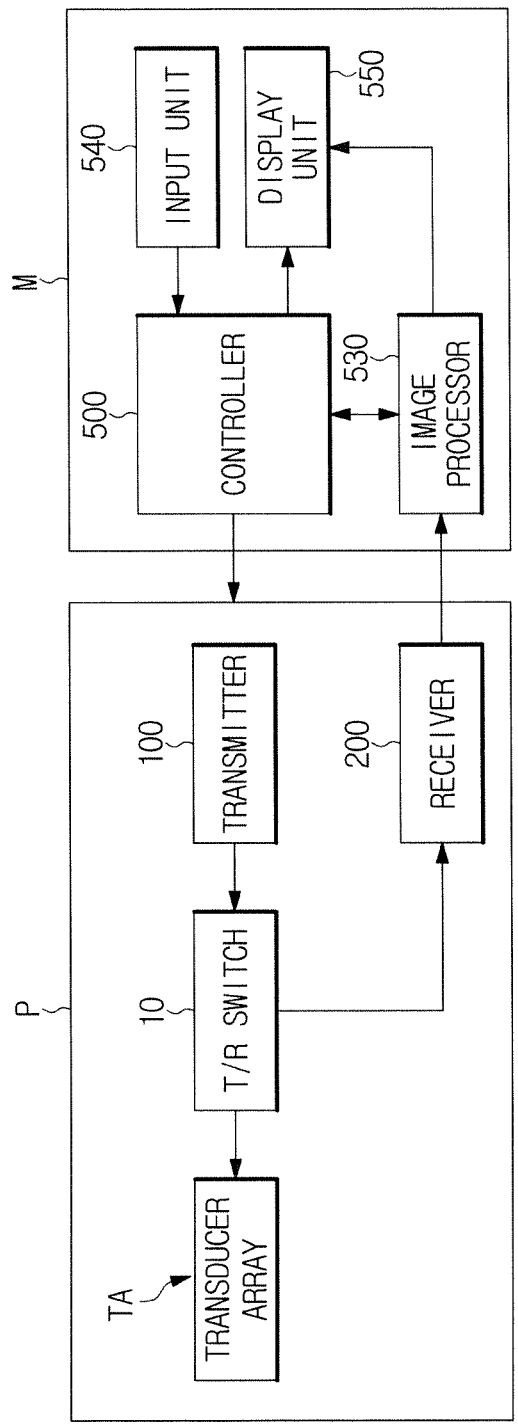
FIG. 2 is a control block diagram of an ultrasonic imaging apparatus according to an embodiment of the present disclosure.
Figure 3:
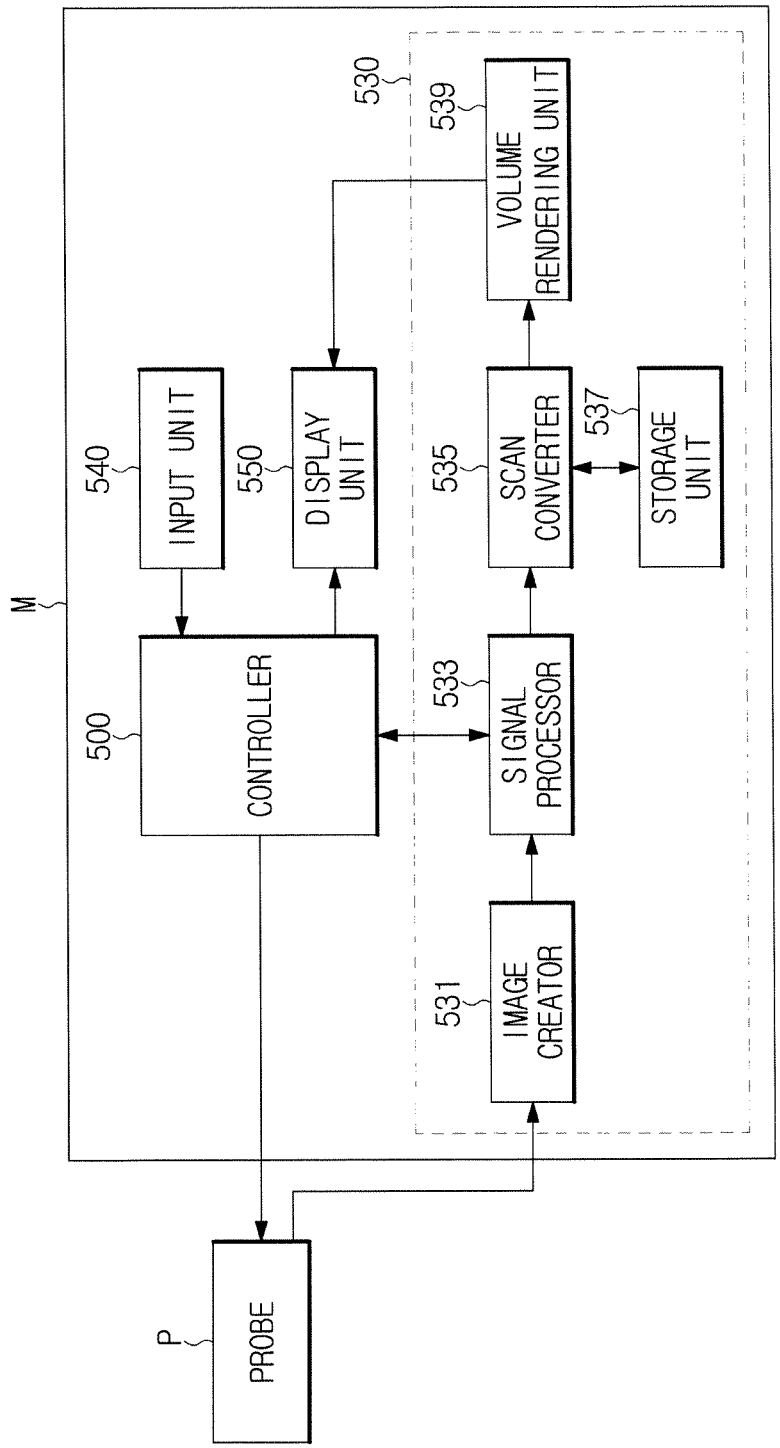
FIG. 3 is a control block diagram showing a configuration of a main body of an ultrasonic imaging apparatus according to an embodiment of the present disclosure.

FIG. 1 shows an external appearance of an ultrasonic imaging apparatus according to an embodiment of the present disclosure, FIG. 2 is a control block diagram of an ultrasonic imaging apparatus according to an embodiment of the present disclosure, FIG. 3 is a control block diagram showing a configuration of a main body of an ultrasonic imaging apparatus according to an embodiment of the present disclosure.

Referring to FIG. 1, an ultrasonic imaging apparatus 1 may include: an ultrasound probe configured to transmit ultrasonic waves to an object, to receive ultrasonic echo signals from the object, and to convert the ultrasonic echo signals into electrical signals; and a main body M connected to the ultrasound probe, including an input unit 540 and a display unit 550, and configured to display ultrasound images. The ultrasound probe P may be connected to the main body M of the ultrasound imaging apparatus 1 through a cable 5 to receive various signals for controlling the ultrasound probe P from the main body M or to transfer analog or digital signals corresponding to ultrasound echo signals received by the ultrasound probe P to the main body M. However, the ultrasound probe P may be a wireless probe that receives/transmits signals from/to the main body M through a network established between the ultrasound probe P and the main body M.

One end of the cable 5 may be connected to the ultrasound probe P, and the other end of the cable 5 may include a connector 6 that can be detachably inserted into at least one of slots 7 formed in the main body M. The main body M and the ultrasound probe P may exchange control commands or data through the cable 5. For example, if a user inputs information about a focal depth, the size or shape of aperture, a steering angle, etc. through the input unit 540, the information may be transferred to the ultrasound probe P through the cable 5 and used for transmission/reception beamforming of a transmitter 100 and a receiver 200 (see FIG. 2). If the ultrasound probe P is a wireless probe, the ultrasound probe P may be connected to the main body M through a wireless network, instead of the cable 5, so that the ultrasound probe P can exchange control commands or data with the main body M through the wireless network. The main body M may include a controller 500, an image processor 530, an input unit 540, and a display unit 550, as shown in FIG. 2. Also, four castors 8 may be installed in the lower part of the main body M in order to move the main body M. Each castor 8 may include a locking element for preventing the castor 8 from rotating to fix the ultrasonic imaging apparatus 1.

The controller 500 may control overall operations of the X-ray imaging apparatus 1. More specifically, the controller 500 may generate control signals for controlling components (for example, the transmitter 100, a Transmission/Reception (T/R) switch 10, the receiver 200, the image processor 530, and the display unit 550 as shown in FIG. 2) of the ultrasonic imaging apparatus 1 to control operations of the components. In the ultrasonic imaging apparatus 1 shown in FIGS. 2 and 3, a transmission/reception beamformer is included in the ultrasound probe P, however, the transmission/reception beamformer may be included in the main body M, instead of the ultrasound probe P.

The controller 500 may calculate a delay profile for a plurality of ultrasound transducer elements configuring a transducer array TA, and calculate time delay values according to differences of distances between the ultrasound transducer elements and a focal point of an object, based on the delay profile. Then, the controller 500 may control the transmission/reception beamformer to generate transmission/reception signals according to the time delay values.

Also, the controller 500 may generate control commands for controlling the individual components of the ultrasonic imaging apparatus 1 according to a user's instruction or command received through the input unit 540 to control the ultrasonic imaging apparatus 1.

The image processor 530 may generate an ultrasound image about a target region inside an object based on an ultrasonic signal focused by the receiver 200.

Referring to FIG. 3, the image processor 530 may include an image creator 531, a signal processor 533, a scan converter 535, a storage unit 537, and a volume rendering unit 539.

The image creator 531 may create a coherent two-dimensional (2D)/three-dimensional (3D) image about a target region inside an object, based on a ultrasonic signal focused by the receiver 200.

The signal processor 533 may convert coherent image data created by the image creator 531 into ultrasound image data according to a diagnosis mode, such as a Brightness mode (B-mode) or a Doppler mode (D-mode). For example, if the diagnosis mode is set to the B-mode, the signal processor 533 may perform processing such as Analog-to-Digital (AD) conversion, and generate ultrasound image data for B-mode image in real time. If the diagnosis mode is set to the D-mode, the signal processor 533 may extract phase-change information from ultrasonic signals, calculate information (for example, velocity, power, or dispersion) of blood flow, etc. corresponding to the individual points of a slice image, and generate ultrasound image data for D-mode image in real time.

The scan converter 535 may convert converted ultrasound image data received from the signal processor 533 or converted ultrasound image data stored in the storage unit 537 into a video signal that can be displayed on the display unit 550, and transmit the video signal to the volume rendering unit 539.

The storage unit 537 may temporarily or non-temporarily store ultrasound image data converted by the signal processor 533.

The volume rendering unit 539 may perform volume-rendering based on the video signal transmitted from the scan converter 535, correct the volume-rendered image data to create a final image, and then transfer the final image to the display unit 550.

The input unit 540 may allow a user to input commands for operations of the ultrasound diagnosis apparatus 1. The user may input an ultrasonic diagnosis start command, a diagnosis mode selection command for selecting a diagnosis mode, such as an Amplitude mode (A-mode), a Brightness mode (B-mode), a Color mode (C-mode), a Doppler mode (D-mode), and a Motion mode (M-mode), or Region Of Interest (ROI) setting information including a size and a location of ROI, through the input unit 540. The input unit 540 may include various means that allows a user to input data, instructions, or commands, such as a keyboard, a mouse, a trackball, a tablet, or a touch screen module. The display unit 550 may display menus or guidance needed for ultrasonic diagnosis, and ultrasound images acquired during ultrasonic diagnosis. The display unit 550 may display ultrasound images about a target region inside an object, created by the image processor 530. An ultrasound image that is displayed on the display unit 550 may be an A-mode ultrasound image, a B-mode ultrasound image, or a 3Dimensional (3D) ultrasound image. The display unit 550 may be one of various displays, such as a Cathode Ray Tube (CRT) and a Liquid Crystal Display (LCD).

The ultrasound probe P according to an embodiment of the present disclosure may include the transducer array TA, the T/R switch 10, the transmitter 100, and the receiver 200, as shown in FIG. 2. The transducer array TA may be installed in one end of the ultrasound probe P. The transducer array TA may be a one-dimensional (1D) array or a two-dimensional (2D) array composed of a plurality of ultrasound transducer elements. The transducer array TA may vibrate by an applied pulse signal or alternating current to generate ultrasonic waves. The generated ultrasonic waves may be transmitted to a target region inside an object. At this time, the ultrasonic waves may be focused on and transmitted to a plurality of target regions inside an object. In other words, the ultrasonic waves may be multi-focused on and transmitted to a plurality of target regions.

The ultrasonic waves generated by the transducer array TA may be reflected from the target region inside the object, and then return to the transducer array TA. The transducer array TA may receive an ultrasonic echo signal reflected from the target region. If an ultrasonic echo signal arrives at the transducer array TA, the transducer array TA may vibrate at a predetermined frequency corresponding to the frequency of the ultrasonic echo signal, and output alternating current of a frequency corresponding to the vibration frequency. Accordingly, the transducer array TA can convert a received ultrasonic echo signal into a predetermined electrical signal. Since each ultrasound transducer element receives an ultrasonic echo signal and outputs an electrical signal, the transducer array TA may output electrical signals of multiple channels.

Each ultrasound transducer may be a magnetostrictive ultrasound transducer using the magnetostrictive effect of a magnetic material, a piezoelectric ultrasound transducer using the piezoelectric effect of a piezoelectric material, or a capacitive micromachined ultrasound transducer (cMUT) that transmits and receives ultrasonic waves using vibration of several hundreds or thousands of micromachined thin films. However, the ultrasound transducer may be any other type ultrasound transducer capable of generating ultrasonic waves according to electrical signals or generating electrical signals according to ultrasonic waves.

For example, each ultrasound transducer element may include a piezoelectric vibrator or a thin film. The piezoelectric vibrator or the thin film may vibrate, when alternating current is applied from a power source, at a predetermined frequency according to the applied alternating current to generate ultrasonic waves of a predetermined frequency according to the vibration frequency. Meanwhile, if an ultrasonic echo signal of a predetermined frequency arrives at the piezoelectric vibrator or the thin film, the piezoelectric vibrator or the thin film may vibrate according to the ultrasonic echo signal to output alternating current of a frequency corresponding to the vibration frequency.

The transmitter 100 may apply transmission pulses to the transducer array TA to enable the transducer array TA to transmit ultrasonic signals to a target region inside an object. The transmitter 100 may include a transmission beamformer and a pulser.

The transmission beamformer may form a transmission signal pattern according to a control signal from the controller 500 of the main body M, and output the transmission signal pattern to the pulser. The transmission beamformer may form a transmission signal pattern based on the time delay values for the ultrasound transducer elements configuring the transducer array TA, the time delay values calculated by the controller 500, and transmit the transmission signal pattern to the pulser.

The receiver 200 may perform predetermined processing on ultrasonic echo signals received by the transducer array TA, and then perform reception beamforming on the processed signals. The receiver 200 may include a reception signal processor and a reception beamformer. Electrical signals converted by the transducer array TA may be input to the reception signal processor. The reception signal processor may amplify the electrical signals converted from the ultrasonic echo signals, and adjust gains of the electrical signals, or compensate for attenuation according to the depths of the electrical signals, before signal-processing or time-delay processing of the electrical signals. More specifically, the reception signal processor may include a Low Noise Amplifier (LNA) to reduce noise of electrical signals received from the transducer array TA, and a Variable Gain Amplifier (VGA) to control gain values according to input signals. The VGA may be Time Gain Compensation (TGA) to compensate for gains according to distances to a focal point, although not limited to this.

The reception beamformer may perform beamforming on the electrical signals received from the reception signal processor. The reception beamformer may enhance the electrical signals received from the reception signal processor by superpositioning the electrical signals. The signals beam-formed by the reception beamformer may be converted into digital signals through an analog-to-digital converter, and then transmitted to the image processor 530 of the main body M. If the analog-to-digital converter is included in the main body M, the analog signals beamformed by the reception beamformer may be transmitted to the main body M, and the analog signals may be converted into digital signals in the main body M. Or, the reception beamformer may be a digital beamformer. If the reception beamformer is a digital beamformer, the digital beamformer may include a storage unit to sample and store analog signals, a sampling period controller to control a sampling period, an amplifier to adjust the magnitudes of samples, an anti-aliasing low-pass filter to prevent aliasing before sampling, a band-pass filter to select a desired frequency band, an interpolation filter to increase a sampling rate upon beamforming, and a high-pass filter to remove DC components or signals of a low-frequency band.

Meanwhile, an ultrasonic imaging apparatus may move through castors installed in the lower part of a main body, as shown in FIG. 1. Also, a portable ultrasonic imaging apparatus can move freely since it has been fabricated in consideration of portability and mobility. When a user moves the ultrasonic imaging apparatus, the user needs to perform a task related to movement of the ultrasonic imaging apparatus, such as plugging out a power cable for supplying power, executing a power-saving function, or unlocking the castors.

If the user moves the ultrasonic imaging apparatus without performing all tasks related to movement of the ultrasonic imaging apparatus, the tasks may be performed during movement, or it may take a long time to acquire ultrasound images at a place to which the ultrasonic imaging apparatus moved. According to an embodiment of the present disclosure, there is provided an ultrasonic imaging apparatus of providing a movement mode to enable a user to certainly perform tasks or functions related to movement of the ultrasonic imaging apparatus when moving the ultrasonic imaging apparatus. Hereinafter, the ultrasonic imaging apparatus will be described in detail.

Figure 4:
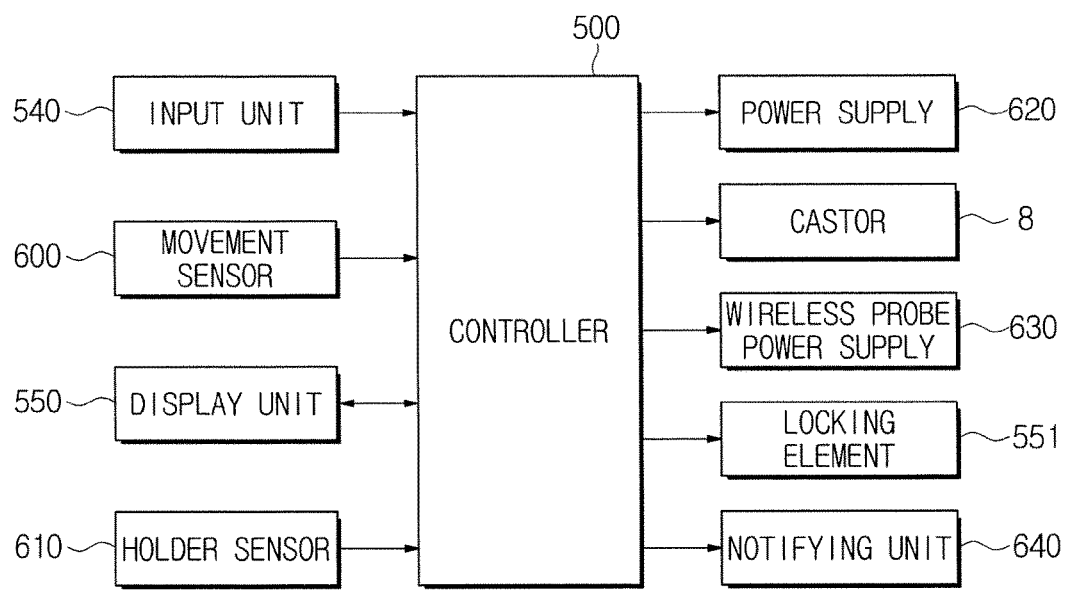
FIG. 4 is a control block diagram showing a configuration related to movement of an ultrasonic imaging apparatus according to an embodiment of the present disclosure.

FIG. 4 is a control block diagram showing a configuration related to movement of an ultrasonic imaging apparatus according to an embodiment of the present disclosure, and FIG. 5 shows functions related to movement of an ultrasonic imaging apparatus according to an embodiment of the present disclosure, which are displayed on a display unit of the ultrasonic imaging apparatus.

As shown in FIG. 4, an ultrasonic imaging apparatus 1 (see FIG. 1) according to an embodiment of the present disclosure may further include components related to movement of the ultrasonic imaging apparatus 1, other than the components shown in FIGS. 2 and 3.

As shown in FIG. 4, the ultrasonic imaging apparatus 1 may include a movement sensor 600 configured to sense movement of the ultrasonic imaging apparatus 1. The movement sensor 600 may be one of various kinds of sensors that can sense movement of the ultrasonic imaging apparatus 1. For example, the movement sensor 600 may be a gyro sensor, an accelerometer, a position sensor, a motion sensor, or an infrared sensor. If the movement sensor 600 senses movement of the ultrasonic imaging apparatus 1, the movement sensor 600 may transfer a signal notifying movement of the ultrasonic imaging apparatus 1 to the controller 500. If the controller 500 receives the signal transferred from the movement sensor 600, the controller 500 may determine that the ultrasonic imaging apparatus 1 starts to move, and display a list of functions or tasks related to movement of the ultrasonic imaging apparatus 1 on the display unit 550.

The input unit 540 may include a separate input device to allow a user to input a command for setting a movement mode of the ultrasonic imaging apparatus 1. For example, the input unit 540 may include a mechanical type button, an electronic type button, or a touch button to allow a user to input a command for setting a movement mode. If a user presses a movement mode setting button, the controller 500 may determine that the ultrasonic imaging apparatus 1 starts to move, like when receiving a signal transferred from the movement sensor 600, and display a list of functions or tasks related to movement of the ultrasonic imaging apparatus 1 on the display unit 550.

That is, when a user moves the ultrasonic imaging apparatus 1 or inputs a command for setting the movement mode through the input unit 540, the ultrasonic imaging apparatus 1 according to the current embodiment may display a list of functions or tasks related to movement of the ultrasonic imaging apparatus 1 on the display unit 550.

As shown in FIG. 4, the ultrasonic imaging apparatus 1 may include a notifying unit 640 configured to notify the start or end of the movement mode through sound or light.

The notifying unit 640 may include a speaker to notify the start or end of the movement mode through predetermined signal sound or voice, a lamp to notify the start or end of the movement mode through light, or a vibrator to notify the start or end of the movement mode through vibrations, although not limited to these. The display unit 550 may also notify a user of the start or end of the movement mode through predetermined text or a predetermined image.

Hereinafter, tasks or functions related to movement of the ultrasonic imaging apparatus 1, which are displayed on the display unit 550, will be described in detail.

As described above, if the movement sensor 600 senses movement of the ultrasonic imaging apparatus 1 or if a user inputs a command for setting the movement mode through the input unit 540, the display unit 550 may display a list of functions or tasks related to movement of the ultrasonic imaging apparatus 1, as shown in FIG. 5. For example, as shown in FIG. 5, the display unit 550 may display a power-off/power-saving function for a wireless probe, a power-off/power-saving function for the ultrasonic imaging apparatus 1, a castor unlock function, a lock function for preventing movement of the display unit 550, a function of recognizing installation of a registered probe, a function of recognizing existence/absence of gel, a shock absorbing function, an ultrasound image storage and transmission function, etc. Also, the display unit 550 may display a list of tasks, such as plugging out a Local Area Network (LAN) line or a power cable or arranging a probe cable, which a user needs to perform. Also, in order for a user to select a desired function to be activated from among the displayed functions, the display unit 500 may display a plurality of checkboxes corresponding to the individual functions. If the user selects a function to be activated, the controller 500 may automatically activate the selected function.

The user can select a desired one of the functions displayed on the display unit 550 through the input unit 540 or by touching, if the display unit 550 is a touch screen, the touch screen. Also, the user may inspect a list of tasks displayed on the display unit 550 to himself/herself perform a task or function required for movement of the ultrasonic imaging apparatus 1.

For example, if the user selects the castor unlock function, the controller 500 may control locking elements of the castors 8 to be unlocked. Also, the user may see castor unlocking displayed on the display unit 550, and release the locked states of the castors 8. That is, the user may select functions that can be automatically activated by the controller 500 to activate the functions automatically, or the user may inspect the list displayed on the display unit 550 and perform a desired function or task.

If the user selects the lock function for preventing movement of the display unit 550, the controller 500 may operate a locking element 551 for preventing folding or unfolding of the display unit 550 in order to prevent the display unit 550 from being folded or unfolded. For example, if the user wants to fold the display unit 550 in order to secure a view, the user may fold the display unit 550 and select the lock function. Then, the locking element 551 may operate in the state in which the display unit 550 is folded, thus preventing the display unit 550 from being again unfolded during movement of the ultrasonic imaging apparatus 1. Also, when the user selects the lock function, the display unit 550 may be automatically folded, and the locking element 551 may operate.

If the user selects the ultrasound image storage and transmission function ("Store & Transmit Images" of FIG. 5), the controller 500 may store a final ultrasound image transmitted to a Picture Archiving and Communication System (PACS) through a communication network before the ultrasonic imaging apparatus 1 moves, and automatically transmit, when the ultrasonic imaging apparatus 1 is again connected to the PACS through the communication network, images acquired after the stored ultrasound image to the PACS. That is, the ultrasound image storage and transmission function enables, when the ultrasonic imaging apparatus 1 is disconnected from the communication network due to movement and then again connected to the communication network, the controller 500 to transmit newly acquired images to the PACS, without again transmitting already transmitted images.

If the user selects the function of recognizing installation of a registered probe, the controller 500 may determine whether the number of probes registered in advance as probes of the ultrasonic imaging apparatus 1 is equal to the number of probes installed in a probe holder, and emit sound or light through the notifying unit 640 if the number of the registered probes is different from the number of the installed probes. The controller 500 may receive a signal notifying that no probe is installed in the probe holder, from a holder sensor 610 installed in the probe holder, and notify the fact through the notifying unit 640.

However, the user may inspect the list to determine whether the number of probes registered in the ultrasonic imaging apparatus 1 is equal to the number of probes installed in the probe holder. Also, if the user selects the function of recognizing existence/absence of gel, the controller 500 may receive a signal notifying that no container including gel is accommodated, from a sensor installed in a holder that accommodates the container, and notify the fact through the notifying unit 640.

If the user selects the power-off/power-saving function for the ultrasonic imaging apparatus 1, the controller 500 may control a power supply 620 to power off the ultrasonic imaging apparatus 1 or to convert to a power-saving mode. Likewise, if the user selects the power-off/power-saving function for the wireless probe, the controller 500 may control a wireless probe power supply 630 to power off the wireless probe or to convert to a power-saving mode.

If the user selects the shock absorbing function ("Shock Absorbing Device" of FIG. 5), the controller 500 may operate protectors installed at several locations of the ultrasonic imaging apparatus 1 in order to provide a buffer function against impacts. For example, the protectors may swell like balloons to provide a buffer function against external impacts. However, there may be provided any other kind of shock absorbing devices as long as they can provide a buffer function against external impacts.

Also, the user may inspect a list of tasks, such as arranging a probe cable or plugging out a LAN line or a power cable, which are displayed on the display unit 550, and perform a task of arranging the probe cable or plugging out the LAN line or the power cable. If the power cable is in a plugged-in state, the controller 500 may notify the fact using sound or light through the notifying unit 640.

Meanwhile, when the user selects desired ones of the displayed functions, the display unit 550 may display a message (for example, "Would You Apply These to Movement Mode?") requesting confirmation on activation of the selected functions before the selected functions are activated. If the user confirms activation of the selected functions, the controller 500 may control operations of components related to the selected functions in order to activate the corresponding functions.

As described above, by displaying various functions or tasks needed for movement of the ultrasonic imaging apparatus 1 on the display unit 550, a user can select and perform necessary functions or tasks that need to be performed, without forgetting them.

Figure 6:
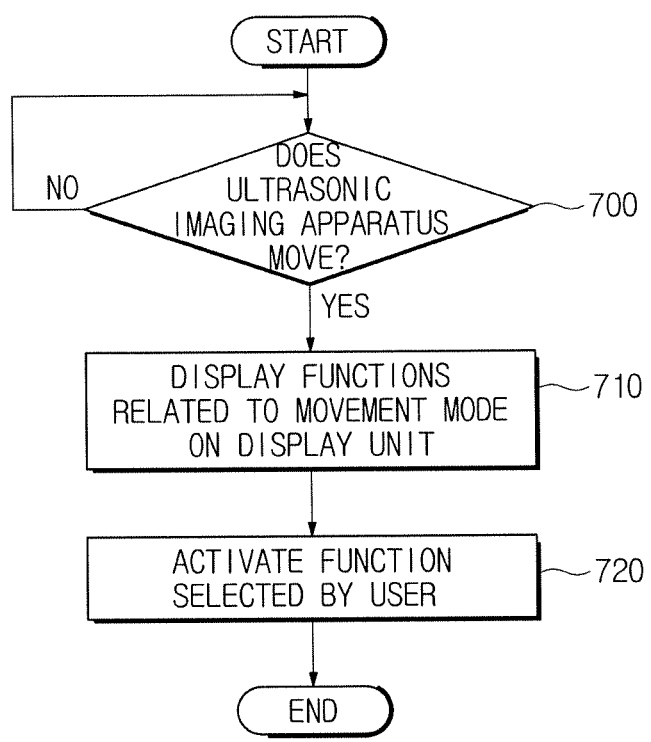
FIG. 6 is a flowchart illustrating a method of controlling an ultrasonic imaging apparatus, according to an embodiment of the present disclosure.

FIG. 6 is a flowchart illustrating a method of controlling an ultrasonic imaging apparatus 1, according to an embodiment of the present disclosure.

Referring to FIGS. 1, 2, 3, 4, and 6, if the ultrasonic imaging apparatus 1 moves in operation 700, the display unit 550 may display functions related to a movement mode, in operation 710. Then, the controller 500 may activate a function selected by a user from among the displayed functions, in operation 720.

If the movement sensor 600 senses movement of the ultrasonic imaging apparatus 1, the movement sensor 600 may transfer a signal notifying movement of the ultrasonic imaging apparatus 1 to the controller 500. If the controller 500 receives the signal from the movement sensor 600, the controller 500 may determine that the ultrasonic imaging apparatus 1 starts to move, and display a list of functions or tasks related to movement of the ultrasonic imaging apparatus 1 on the display unit 550.

The input unit 540 may include a separate input device to allow a user to input a command for setting a movement mode of the ultrasonic imaging apparatus 1. For example, the input unit 540 may include a movement mode setting button to allow a user to input a command for setting a movement mode. If a user presses the movement mode setting button, the controller 500 may determine that the ultrasonic imaging apparatus 1 starts to move, like when receiving a signal transferred from the movement sensor 600, and display a list of functions or tasks related to movement of the ultrasonic imaging apparatus 1 on the display unit 550.

That is, when a user moves the ultrasonic imaging apparatus 1 or inputs a command for setting a movement mode through the input unit 540, the ultrasonic imaging apparatus 1 according to the current embodiment may display a list of functions or tasks related to movement of the ultrasonic imaging apparatus 1 on the display unit 550.

As described above, if the movement sensor 600 senses movement of the ultrasonic imaging apparatus 1 or if a user inputs a command for setting the movement mode through the input unit 540, the display unit 550 may display a list of functions or tasks related to movement of the ultrasonic imaging apparatus 1, as shown in FIG. 5. For example, as shown in FIG. 5, the display unit 550 may display a power-off/power-saving function for a wireless probe, a power-off/power-saving function for the ultrasonic imaging apparatus 1, a castor unlock function, a lock function for preventing movement of the display unit 550, a function of recognizing installation of a registered probe, a function of recognizing existence/absence of gel, a shock absorbing function, an ultrasound image storage and transmission function, etc. Also, the display unit 550 may display a list of tasks, such as plugging out a Local Area Network (LAN) line or a power cable or arranging a probe cable, which a user needs to perform. Also, in order for a user to select a desired function to be activated from among the displayed functions, the display unit 500 may display a plurality of checkboxes corresponding to the individual functions. If the user selects a function to be activated, the controller 500 may automatically activate the selected function. The user can select a desired one of the functions displayed on the display unit 550 through the input unit 540 or by touching, if the display unit 550 is a touch screen, the touch screen. Also, the user may see a list of tasks displayed on the display unit 550, and himself/herself perform a task or function required for movement of the ultrasonic imaging apparatus 1.

For example, if the user selects the castor unlock function, the controller 500 may control locking elements of the castors 8 to be unlocked. Also, the user may see castor unlocking displayed on the display unit 550, and release the locked states of the castors 8. That is, the user may select functions that can be automatically activated by the controller 500 to activate the functions automatically, or the user may inspect the list displayed on the display unit 550 and perform a desired function or task.

If the user selects the lock function for preventing movement of the display unit 550, the controller 500 may operate a locking element 551 for preventing folding or unfolding of the display unit 550 in order to prevent the display unit 550 from being folded or unfolded. For example, if the user wants to fold the display unit 550 in order to secure a view, the user may fold the display unit 550 and select the lock function. Then, the locking element 551 may operate in the state in which the display unit 550 is folded, thus preventing the display unit 550 from being unfolded during movement of the ultrasonic imaging apparatus 1. Also, when the user selects the lock function, the display unit 550 may be automatically folded, and the locking element 551 may operate.

If the user selects the ultrasound image storage and transmission function ("Store & Transmit Images" of FIG. 5), the controller 500 may store a final ultrasound image transmitted to the PACS through a communication network before the ultrasonic imaging apparatus 1 moves, and automatically transmit, when the ultrasonic imaging apparatus 1 is again connected to the PACS through the communication network, images acquired after the stored ultrasound image to the PACS. That is, the ultrasound image storage and transmission function enables, when the ultrasonic imaging apparatus 1 is disconnected from the communication network due to movement and then again connected to the communication network, the controller 500 to transmit newly acquired images to the PACS, without again transmitting already transmitted images.

If the user selects the function of recognizing installation of a registered probe, the controller 500 may determine whether the number of probes registered in advance as probes of the ultrasonic imaging apparatus 1 is equal to the number of probes installed in a probe holder, and emit sound or light through the notifying unit 640 if the number of the registered probes is different from the number of the installed probes. The controller 500 may receive a signal notifying that no probe is installed in the probe holder, from a holder sensor 610 installed in the probe holder, and notify the fact through the notifying unit 640.

However, the user may inspect the list to determine whether the number of probes registered in the ultrasonic imaging apparatus 1 is equal to the number of probes installed in the probe holder. Also, if the user selects the function of recognizing existence/absence of gel, the controller 500 may receive a signal notifying that no container that contains gel is accommodated, from a sensor installed in a holder that accommodates the container, and notify the fact through the notifying unit 640.

If the user selects the power-off/power-saving function for the ultrasonic imaging apparatus 1, the controller 500 may control a power supply 620 to power off the ultrasonic imaging apparatus 1 or to convert to a power-saving mode. Likewise, if the user selects the power-off/power-saving function for the wireless probe, the controller 500 may control a wireless probe power supply 630 to power off the wireless probe or to convert to a power-saving mode.

If the user selects the shock absorbing function ("Shock Absorbing Device" of FIG. 5), the controller may operate protectors installed at several locations of the ultrasonic imaging apparatus 1 in order to provide a buffer function against impacts. For example, the protectors may swell like balloons to provide a buffer function against external impacts. However, there may be provided any other kind of shock absorbing devices as long as they can provide a buffer function against external impacts.

Also, the user may inspect a list of tasks, such as arranging a probe cable or plugging out a LAN line or a power cable, which is displayed on the display unit 550, and perform a task of arranging the probe cable or plugging out the LAN line or the power cable. If the power cable is in a plugged-in state, the notifying unit 640 may notify the fact through sound or light.

Meanwhile, when the user selects desired ones of the displayed functions, the display unit 550 may display a message (for example, "Would You Apply These to Movement Mode ?") requesting confirmation on activation of the selected functions before the selected functions are activated. If the user confirms activation of the selected functions, the controller 500 may control operations of components related to the selected functions in order to activate the corresponding functions.

As described above, by displaying various functions or tasks needed for movement of the ultrasonic imaging apparatus 1 on the display unit 550, a user can select and perform necessary functions or tasks that need to be performed, without forgetting them.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:
1. An ultrasonic imaging apparatus comprising:
  an ultrasound probe configured to:
    transmit ultrasonic waves to an object;
    receive ultrasonic echo signals from the object; and
    convert the ultrasonic echo signals into electrical signals;
  a main body connected to the ultrasound probe and including:

a sensor configured to sense movement of the ultrasonic imaging apparatus; and
an input configured to receive a command for setting a movement mode of the ultrasonic imaging apparatus;
a display configured to display functions related to the movement of the ultrasonic imaging apparatus when the movement of the ultrasonic imaging apparatus is sensed by the sensor or the command for setting the movement mode is inputted using the input; and
a controller configured to activate a function selected by a user among the one or more functions displayed on the display,
wherein the functions include a castor unlock function, a lock function for preventing movement of the display, a function of recognizing existence/absence of gel, a shock absorbing function, and an ultrasound image storage and transmission function, and
wherein, when the ultrasound image storage and transmission function is selected by the user, the controller stores at least one image transmitted to a Picture Archiving and Communication System (PACS) before the ultrasonic imaging apparatus moves, and transmits images acquired after the stored image to the PACS if the ultrasonic imaging apparatus is again connected to the PACS.

2. The ultrasonic imaging apparatus according to claim 1, wherein the sensor includes at least one of an accelerometer, a gyro sensor, a position sensor, a motion sensor, or an infrared sensor, which is configured to sense the movement of the ultrasonic imaging apparatus.

3. The ultrasonic imaging apparatus according to claim 1, wherein the input comprises at least one of a mechanical type button, an electronic type button, or a touch button to allow the user to input the command for setting the movement mode.

4. The ultrasonic imaging apparatus according to claim 1, wherein the main body further comprises an output configured to notify the movement of the ultrasonic imaging apparatus when the ultrasonic imaging apparatus moves, so that the output and the display are separately connected to the ultrasound probe, and
wherein the output comprises at least one of a speaker configured to notify the movement of the ultrasonic imaging apparatus using sound or a lamp configured to notify the movement of the ultrasonic imaging apparatus using light.

5. The ultrasonic imaging apparatus according to claim 1, wherein the display displays a text or an image to notify the movement of the ultrasonic imaging apparatus when the ultrasonic imaging apparatus moves.

6. The ultrasonic imaging apparatus according to claim 1, further comprising a holder in which a registered probe and the gel are contained,
wherein the holder comprises a sensor configured to sense the registered probe and the gel.

7. The ultrasonic imaging apparatus according to claim 1, wherein when the ultrasonic imaging apparatus moves, the display displays a list of tasks needed for the movement of the ultrasonic imaging apparatus.

8. The ultrasonic imaging apparatus according to claim 7, wherein the list of tasks includes a task of plugging out a Local Area Network (LAN) line or a power cable or a task of arranging a probe cable.

9. The ultrasonic imaging apparatus according to claim 1, wherein if the function is selected by the user from among the functions displayed on the display, the display displays a message requesting confirmation on activation of the selected function.

10. A method of controlling an ultrasonic imaging apparatus, which includes: an ultrasound probe configured to transmit ultrasonic waves to an object, to receive ultrasonic echo signals from the object, and to convert the ultrasonic echo signals into electrical signals; and a main body connected to the ultrasound probe, the method comprising:
displaying functions related to movement of the ultrasonic imaging apparatus on a display when the movement of the ultrasonic imaging apparatus is sensed by a sensor or a command for setting a movement mode is inputted using an input; and
activating, by a controller, a function selected by a user from among the functions displayed on the display,
wherein the functions include a castor unlock function, a lock function for preventing movement of the display, a function of recognizing existence/absence of gel, a shock absorbing function, and an ultrasound image storage and transmission function,
wherein when the ultrasound image storage and transmission function is selected by the user, storing at least one image transmitted to a Picture Archiving and Communication System (PACS) before the ultrasonic imaging apparatus moves, and transmitting images acquired after the stored image to the PACS if the ultrasonic imaging apparatus is again connected to the PACS.

* * * * *